(12) United States Patent
Yamamoto et al.

(10) Patent No.: US 11,323,598 B2
(45) Date of Patent: May 3, 2022

(54) IMAGE PICKUP APPARATUS, METHOD OF MANUFACTURING IMAGE PICKUP APPARATUS, AND ENDOSCOPE

(71) Applicant: OLYMPUS CORPORATION, Tokyo (JP)

(72) Inventors: Ken Yamamoto, Nagano (JP); Takatoshi Igarashi, Hachioji (JP); Takuro Suyama, Ina (JP); Kazuhiro Yoshida, Okaya (JP); Kensuke Suga, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 57 days.

(21) Appl. No.: 16/924,280

(22) Filed: Jul. 9, 2020

(65) Prior Publication Data
US 2020/0344386 A1    Oct. 29, 2020

Related U.S. Application Data

(63) Continuation of application No. PCT/JP2018/000179, filed on Jan. 9, 2018.

(51) Int. Cl.
*H04N 5/225*    (2006.01)
*A61B 1/00*     (2006.01)
(Continued)

(52) U.S. Cl.
CPC ......... *H04N 5/2253* (2013.01); *A61B 1/0011* (2013.01); *A61B 1/051* (2013.01);
(Continued)

(58) Field of Classification Search
CPC .............. A61B 1/00096; A61B 1/0011; A61B 1/00114; A61B 1/051; G02B 23/2484;
(Continued)

(56) References Cited

U.S. PATENT DOCUMENTS 4,918,521 A    4/1990   Yabe et al.
5,662,584 A *  9/1997   Hori .................. A61B 1/00096
                                                    348/65

(Continued)

FOREIGN PATENT DOCUMENTS

JP    S63-313970 A    12/1988
JP    2002-291693 A   10/2002
(Continued)

OTHER PUBLICATIONS

International Seach Report dated Feb. 13, 2018 issued in PCT/JP2018/000179.

*Primary Examiner* — Peter D Le
(74) *Attorney, Agent, or Firm* — Scully, Scott, Murphy & Presser, P.C.

(57) ABSTRACT

An image pickup apparatus disposed in an endoscope includes an optical unit in which a plurality of optical members are stacked, an image pickup unit including an image pickup device and a plurality of semiconductor devices, mold resin covering the optical unit and the image pickup unit, and a wiring board bonded to the image pickup unit, in which a recess is provided on an outer peripheral surface of the mold resin.

13 Claims, 10 Drawing Sheets

(51) Int. Cl.
*A61B 1/05* (2006.01)
*G02B 23/24* (2006.01)
*H01L 27/146* (2006.01)

(52) U.S. Cl.
CPC .... *G02B 23/2484* (2013.01); *H01L 27/14618* (2013.01); *H01L 27/14625* (2013.01); *H04N 2005/2255* (2013.01)

(58) Field of Classification Search
CPC ........ H01L 27/14618; H01L 27/14625; H04N 2005/2255; H04N 5/2253
See application file for complete search history.

(56) References Cited

U.S. PATENT DOCUMENTS

| | | | | |
|---|---|---|---|---|
| RE37,356 E | * | 9/2001 | Hori | A61B 1/00188 348/65 |
| 10,321,806 B2 | * | 6/2019 | Iizuka | A61B 1/00096 |
| 10,498,940 B2 | * | 12/2019 | Jang | A61B 1/00177 |
| 11,096,559 B2 | * | 8/2021 | Kitano | A61B 1/00096 |
| 2001/0012053 A1 | * | 8/2001 | Nakamura | G02B 23/2484 348/45 |
| 2001/0052930 A1 | * | 12/2001 | Adair | A61B 1/00016 348/65 |
| 2002/0076180 A1 | * | 6/2002 | Miyano | A61B 1/00096 385/117 |
| 2002/0080233 A1 | * | 6/2002 | Irion | H04N 5/2251 348/65 |
| 2007/0019952 A1 | * | 1/2007 | Fujimori | H01L 27/14618 396/529 |
| 2011/0074941 A1 | * | 3/2011 | Takasaki | A61B 1/051 348/68 |
| 2011/0175990 A1 | * | 7/2011 | Sato | H04N 7/183 348/65 |
| 2012/0200683 A1 | * | 8/2012 | Oshima | G06T 11/60 348/65 |
| 2015/0065796 A1 | * | 3/2015 | Iwane | B23K 1/012 600/109 |
| 2015/0238069 A1 | * | 8/2015 | Osada | G02B 23/2423 600/109 |
| 2015/0245763 A1 | * | 9/2015 | Kido | A61B 1/051 600/109 |
| 2015/0257631 A1 | * | 9/2015 | Sasamoto | G01J 1/0411 250/216 |
| 2016/0363757 A1 | * | 12/2016 | Imai | A61B 1/00087 |
| 2017/0059848 A1 | * | 3/2017 | Haraguchi | A61B 1/00096 |
| 2017/0108691 A1 | * | 4/2017 | Kitano | H04N 5/2256 |
| 2017/0307872 A1 | * | 10/2017 | Hatase | A61B 1/0661 |
| 2018/0242826 A1 | * | 8/2018 | Shimohata | A61B 1/0661 |
| 2020/0100655 A1 | * | 4/2020 | Morishima | A61B 1/0055 |

FOREIGN PATENT DOCUMENTS

| | | |
|---|---|---|
| JP | 2004-159970 A | 6/2004 |
| JP | 2005-334509 A | 12/2005 |
| JP | 2011-200398 A | 10/2011 |
| JP | 2013-030593 A | 2/2013 |
| JP | 2015-066300 A | 4/2015 |
| JP | 2017-103478 A | 6/2017 |
| WO | WO 2017/073440 A1 | 5/2017 |

* cited by examiner

IMAGE PICKUP APPARATUS, METHOD OF MANUFACTURING IMAGE PICKUP APPARATUS, AND ENDOSCOPE

CROSS REFERENCE TO RELATED APPLICATION

This application is a continuation application of PCT/JP2018/000179 filed on Jan. 9, 2018, the entire contents of which are incorporated herein by this reference.

BACKGROUND OF THE INVENTION

1. Field of the Invention

The present invention relates to an image pickup apparatus including a stacked element in which a plurality of semiconductor devices are stacked, and disposed in a distal end portion of an endoscope, a method of manufacturing the image pickup apparatus including the stacked element, in which the plurality of semiconductor devices are stacked, disposed in the distal end portion of the endoscope, and an endoscope including, in a distal end portion thereof, an image pickup apparatus including a stacked element in which a plurality of semiconductor devices are stacked.

2. Description of the Related Art

An image pickup signal to be outputted by an image pickup device disposed in a distal end portion of an endoscope is subjected to primary processing by a plurality of electronic components.

Japanese Patent Application Laid-Open Publication No. 2005-334509 discloses an endoscope including an image pickup apparatus to which an image pickup signal subjected to primary processing by a plurality of electronic components mounted on a wiring board is transmitted via an electrical cable.

Japanese Patent Application Laid-Open Publication No. 2013-30593 discloses a stacked element in which a plurality of semiconductor devices are stacked and bonded by a through wiring to house the plurality of semiconductor devices in a small space and reduce a parasitic capacitance by the wiring.

International Publication No. 2017/073440 discloses an endoscope that implements significant miniaturization and high functionality of an image pickup apparatus by using a stacked element.

An electrical cable configured to transmit an image pickup signal and supply driving power is connected to the image pickup apparatus. In the image pickup apparatus including the stacked element, the stacked element and the electrical cable are electrically connected to each other.

SUMMARY OF THE INVENTION

An image pickup apparatus according to an aspect of the present invention includes an optical unit in which a plurality of optical members are stacked, an image pickup unit including an image pickup device and a plurality of semiconductor devices, mold resin covering a composite unit including the optical unit and the image pickup unit, and a wiring board or an electrical cable bonded to the image pickup unit, in which at least one locking member including at least one of a recess or a protrusion is provided on an outer peripheral surface of the mold resin.

A method of manufacturing an image pickup apparatus in an endoscope according to still another aspect of the present invention includes producing an optical unit in which a plurality of optical members are stacked and an image pickup unit including an image pickup device and a plurality of semiconductor devices, arranging a composite unit including the optical unit and the image pickup unit within a mold, filling the mold with mold resin, removing the composite unit covered with the mold resin from the mold, fixing a jig to the composite unit covered with the mold resin, bonding the image pickup unit in the composite unit, covered with the mold resin, held by the jig and a wiring board or an electrical cable to each other, removing the jig fixed to the composite unit covered with the mold resin, providing at least one locking member including at least one of a recess or a protrusion on an outer peripheral surface of the mold resin, and fitting the locking member to the jig when the jig is fixed to the mold resin.

An endoscope according to yet another aspect of the present invention includes an image pickup apparatus. The image pickup apparatus includes an optical unit in which a plurality of optical members are stacked, an image pickup unit including an image pickup device and a plurality of semiconductor devices, mold resin covering a composite unit including the optical unit and the image pickup unit, and a wiring board or an electrical cable bonded to the image pickup unit, in which at least one locking member including at least one of a recess or a protrusion is provided on an outer peripheral surface of the mold resin.

DETAILED DESCRIPTION OF THE PREFERRED EMBODIMENTS

<Configuration of Endoscope in Embodiment>

Figure 1:
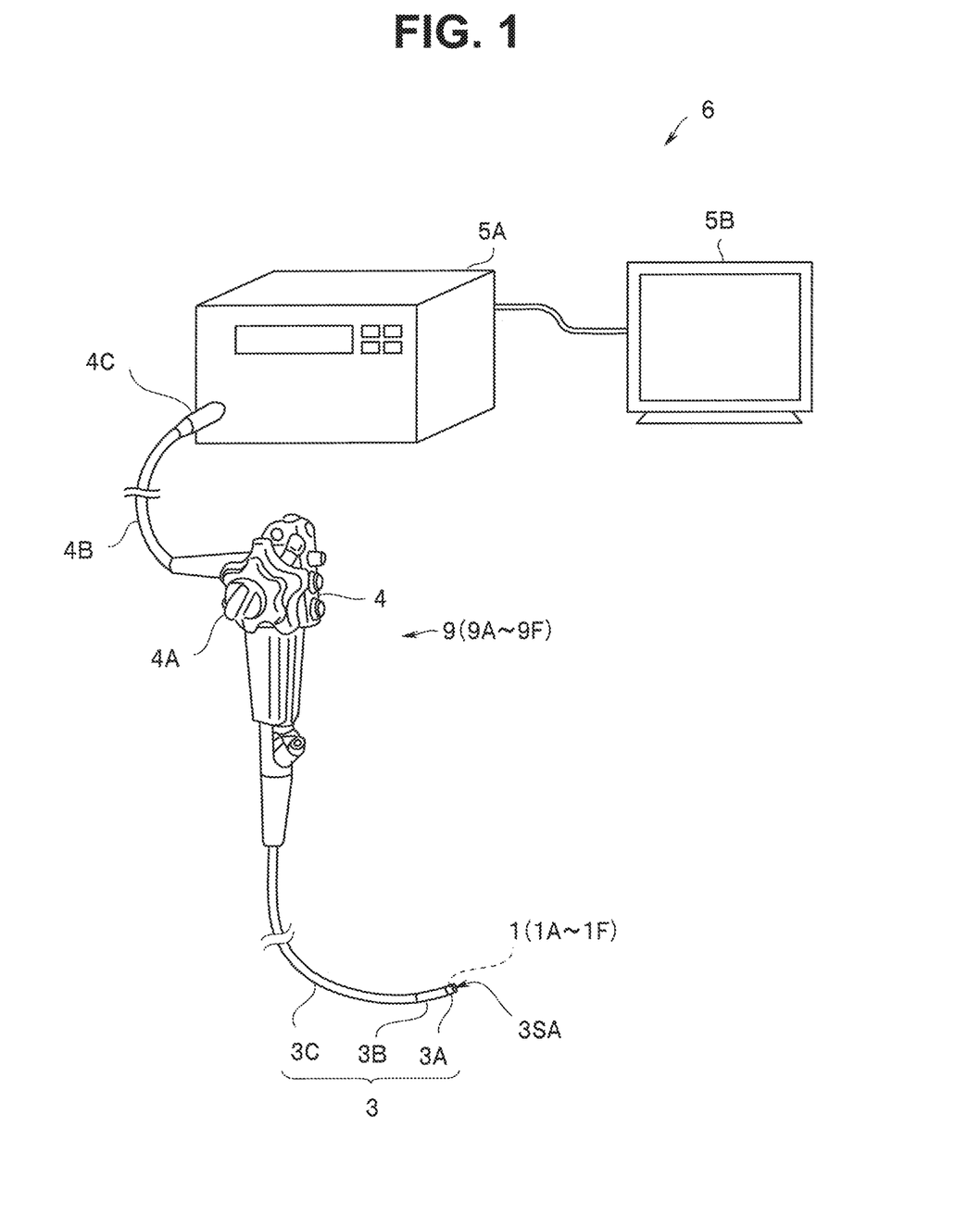
FIG. 1 is a perspective view of an endoscope according to a first embodiment.

As illustrated in FIG. 1, an endoscope 9 according to an embodiment, together with a processor 5A and a monitor 5B, constitutes an endoscope system 6. The endoscope includes an image pickup apparatus 1 in a distal end portion 3A of an insertion section 3.

The endoscope 9 includes the insertion section 3, a grasping section 4 disposed on a proximal end portion side of the insertion section 3, a universal cord 4B provided to extend from the grasping section 4, and a connector 4C disposed on a proximal end portion side of the universal cord 4B. The insertion section 3 includes the distal end portion 3A in which the image pickup apparatus 1 is disposed, a bending portion 3B provided to extend on a proximal end side of the distal end portion 3A, being bendable, and configured to change a direction of the distal end portion 3A, and a flexible portion 3C provided to extend on a proximal end side of the bending portion 3B. An angle knob 4A, which turns, as an operation portion configured to operate the bending portion 3B by an operator is disposed in the grasping section 4.

The universal cord 4B is connected to the processor 5A via the connector 4C. The processor 5A controls the entire endoscope system 6, and performs signal processing for an image pickup signal to be outputted by the image pickup apparatus 1 and outputs the image pickup signal as an image signal. The monitor 5B displays the image signal to be outputted by the processor 5A as an endoscope image. Note that although the endoscope 9 is a flexible endoscope, the endoscope according to the present invention may be a rigid endoscope, and use of the endoscope 9 may be medical use or industrial use.

First Embodiment

Figure 2:
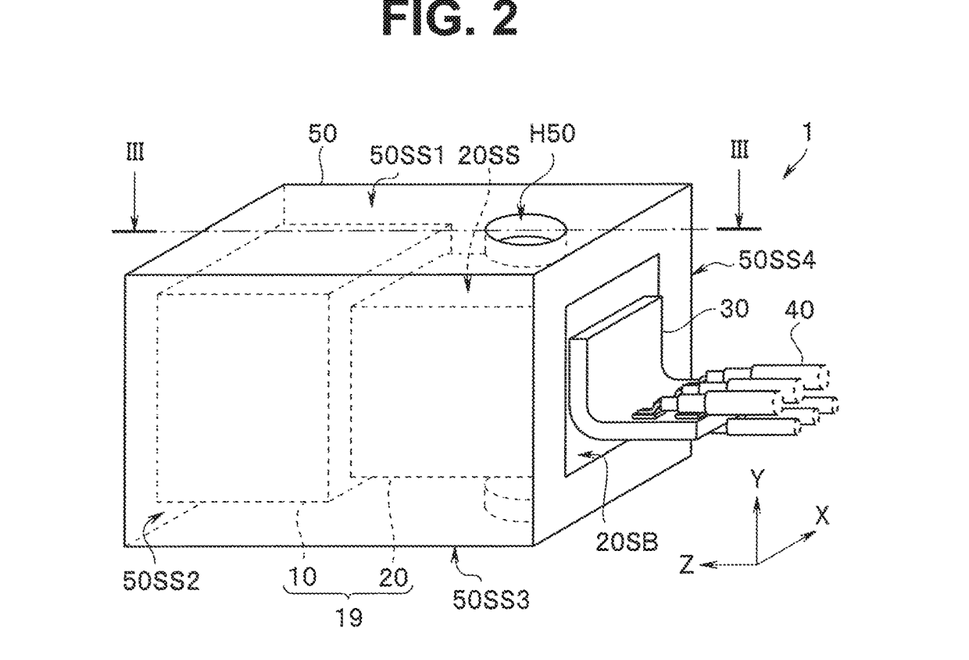
FIG. 2 is a perspective view of an image pickup apparatus according to the first embodiment.
Figure 3:
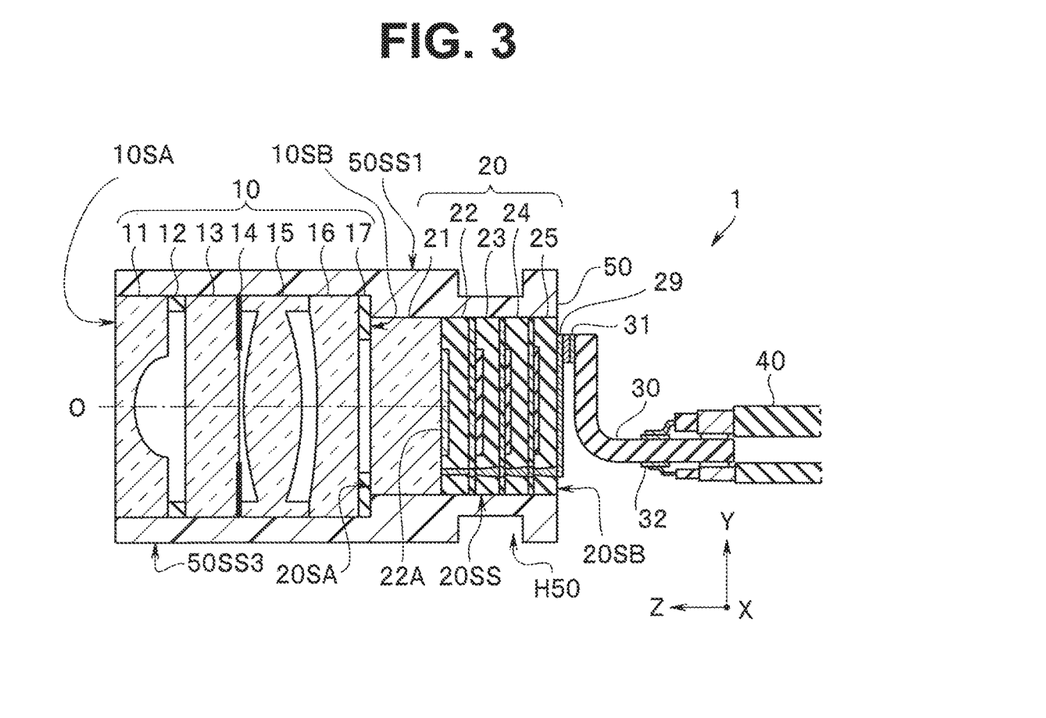
FIG. 3 is a cross-sectional view along a line III-III illustrated in FIG. 2 of the image pickup apparatus according to the first embodiment.
Figure 4:
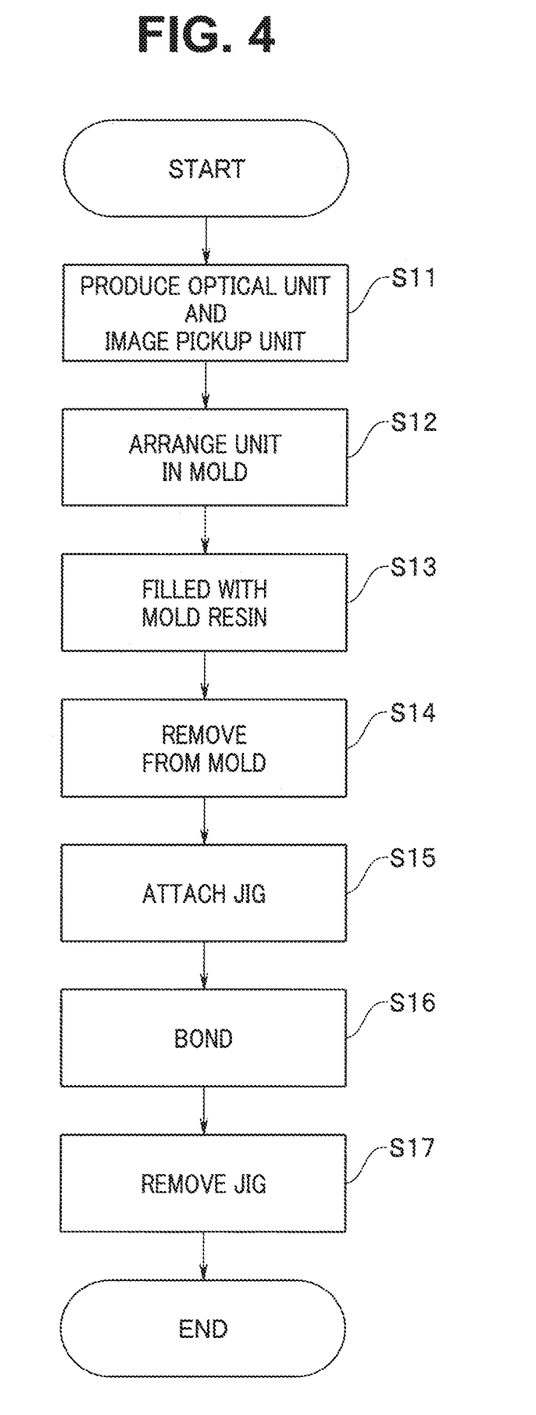
FIG. 4 is a flowchart illustrating a method of manufacturing the image pickup apparatus according to the first embodiment.

An image pickup apparatus 1 according to the present embodiment illustrated in FIGS. 2 to 4 includes an optical unit 10, an image pickup unit 20, mold resin 50, a wiring board 30, and an electrical cable 40. In the image pickup apparatus 1, the image pickup unit 20 receives image pickup light collected by the optical unit 10 and converts the image pickup light into an electrical signal, further subjects the electrical signal to primary processing, and outputs the electrical signal to the processor 5A via the wiring board 30 and the electrical cable 40.

In the following description, it should be noted that drawings based on each of embodiments are schematic and a relationship between a thickness and a width of each of sections, a ratio of thicknesses of the sections, a relative angle, and the like respectively differ from actual ones, and sections that differ in dimensional relationship or ratio may also be included among the drawings. Illustration of some of components and assignment of reference numerals may be omitted. A direction of an object is referred to as a forward direction.

The optical unit 10 in which a plurality of optical members 11 to 17 are stacked includes an incidence surface 10SA on which light is incident and an emission surface 10SB on an opposite side to the incidence surface 10SA.

The optical members 11, 15, and 16 are each a lens, the optical members 12 and 17 are each a spacer, the optical member 13 is a filter, and the optical member 14 is an aperture. The number of optical members, an arrangement of the optical members, and the like are set depending on a specification of the optical unit.

The image pickup unit 20 includes a cover glass 21, an image pickup device 22, and a stacked element in which a plurality of semiconductor devices 23, 24, and 25 are stacked. The image pickup device 22 is, for example, a parallel plate chip, and the image pickup unit 20 produced using a wafer level method is a rectangular parallelepiped having a front surface 20SA, a rear surface 20SB on an opposite side to the front surface 20SA, and four side surfaces 20SS, as described below. The image pickup unit 20 is arranged with the front surface 20SA facing the emission surface 10SB of the optical unit 10.

The image pickup device 22 includes a light receiving section 22A including a CCD or a CMOS, and the light receiving section 22A is connected to a through wiring. The image pickup device 22 may be a front surface irradiation-type image sensor and a rear surface irradiation-type image sensor.

The cover glass 21 is bonded to the image pickup device 22 using an adhesive agent (not illustrated). Note that although the cover glass 21 protects the light receiving section 22A in a manufacturing process, the cover glass 21 is not an essential component in the image pickup unit 20. The cover glass 21 is not limited to a parallel plate made of glass, but may be a resin plate, a ceramic plate, or the like having a high light transmittance of image pickup light.

The semiconductor devices 23 to 25 in the image pickup unit 20 each have a through wiring, and are electrically connected to one another. The image pickup device 22 and the semiconductor devices 23 to 25 are connected to one another by a solder bump by an electroplating method or a solder bonding portion including a solder paste film by printing or the like.

Sealing resin is disposed among the image pickup device 22 and the semiconductor devices 23 and 25. The image pickup unit 20 subjects an image pickup signal to be outputted by the image pickup device 22 to primary processing, and processes a control signal for controlling the image pickup device 22. For example, the semiconductor devices 23 to 25 each include an AD conversion circuit, a memory, a transmission output circuit, a filter circuit, a thin film capacitor, a thin film inductor, and the like. The number of elements included in the image pickup unit 20, including the image pickup device 22, is three or more and ten or less, for example. The image pickup apparatus 1 including the stacked element is small in size and is highly functional.

A plurality of external electrodes 29 are disposed on the rear surface 20SB (a rear surface of the semiconductor device 25 stacked in a rearmost portion) of the image pickup unit 20. The external electrode 29 is electrically connected to the light receiving section 22A by a through wiring. The external electrode 29 includes a barrier Ni layer and an Au layer disposed on a wiring pattern made of Cu, for example.

The external electrode 29 is bonded to a first electrode 31 in the wiring board 30. The electrical cable 40 is bonded to a second electrode connected to the first electrode 31 by a wiring pattern (not illustrated). Note that the electrical cable 40 may be bonded to the external electrode 29 in the image pickup unit 20. The wiring hoard 30 or the electrical cable 40 is bonded to the image pickup unit 20.

The mold resin 50 covers respective outer peripheral surfaces of the optical unit 10 and the image pickup unit 20. For example, the mold resin 50 having fluidity is poured (filled) into a mold 60 (see FIGS. 5 to 7) and solidified.

In the image pickup apparatus 1, recesses H50 of the mold resin 50 as locking members are respectively provided at positions on both sides with an optical axis being interposed between the recesses H50. The recesses H50 are fitted to a jig 70 (see FIGS. 8 and 9) in a bonding process for bonding the wiring board 30, as described below.

Although the image pickup apparatus 1 includes a stacked element that is not high in mechanical strength, the respective outer peripheral surfaces of the optical unit 10 and the image pickup unit 20 are covered with and protected by the mold resin 50. The mold resin 50 is provided with the recess H50. Accordingly, when a jig having a protrusion to be fitted to the recess H50 is used, the image pickup unit 20 is stably and safely held in the jig. Since the image pickup unit 20 is stably held in the jig in the image pickup apparatus 1, bonding work of the wiring board 30 is easy, and there is no risk that the image pickup unit 20 may be damaged or deteriorate in reliability, as described below.

<Method of Manufacturing Image Pickup Apparatus>

A method of manufacturing the image pickup apparatus 1 will be simply described with reference to a flowchart illustrated in FIG. 4.

<Step S11> Process for Producing Optical Unit and Image Pickup Unit

The optical unit 10 and the image pickup unit 20 are produced using a wafer level method in the wafer level method, a plurality of units are efficiently produced by cutting a bonding wafer obtained by bonding a plurality of wafers.

A plurality of optical wafers each including a plurality of optical members 21 to 27 are produced. For example, the optical member 11 is subjected to curing processing with transparent resin disposed in a glass wafer and an outer surface shape defined by a lens mold form. The optical wafer may be produced by sandwiching a resin wafer between two lens mold forms and molding the resin wafer while applying heat.

An optical bonding wafer obtained by bonding a plurality of optical wafers is cut, and is diced into a plurality of rectangular parallelepiped-shaped optical units 10. Four side surfaces of the optical unit 10 produced using a wafer level method are each a cut surface. The cutting is generally blade dicing, but may be laser dicing or plasma dicing.

On the other hand, an image pickup wafer including a plurality of image pickup devices 22 and a plurality of semiconductor wafers each including a plurality of semiconductor devices 23 to 25 are produced.

For example, in the image pickup wafer, a plurality of light receiving sections 22A or the like are disposed using a known semiconductor manufacturing technique in a silicon wafer or the like. In the image pickup wafer, a peripheral circuit configured to subject an output signal of the light receiving section 22A to primary processing and process a driving control signal may be formed. In the image pickup wafer, a cover glass wafer configured to protect the light receiving section 22A is preferably made to adhere to the image pickup wafer with an adhesive layer (not illustrated) before a through wiring is formed from a rear surface of the image pickup wafer.

The image pickup wafer to which the cover glass wafer is made to adhere and the plurality of semiconductor wafers each including the semiconductor devices 23 to 25 are stacked using sealing resin, to produce a semiconductor bonding wafer. The sealing resin may be injected from a side surface of the bonding wafer after bonding, or may be disposed in a stacked arrangement. The sealing resin is preferably excellent in moisture resistance and substantially the same in thermal expansion coefficient as the semiconductor device 23 or the like.

The semiconductor bonding water is cut such that four sides of the substantially rectangular light receiving section 22A in the image pickup device 22 are respectively parallel to four sides, in a rectangular cross section perpendicular to an optical axis O, of the stacked element and is diced into a plurality of rectangular parallelepiped-shaped image pickup units 20. Four side surfaces of the image pickup unit 20 produced using a wafer level method are each a cut surface.

Note that a corner portion parallel to the optical axis O may be chamfered after the optical unit 10 and the image pickup unit 20 are cut, to make a cross section in the direction perpendicular to the optical axis hexagonal, or the corner portion may be curved.

In other words, although the unit produced using a wafer level method is a rectangular parallelepiped, the term "rectangular parallelepiped" in the description of the present invention also includes a substantially rectangular parallelepiped, a corner portion of which is chamfered or is curved.

The optical unit 10 is bonded to a front surface of the image pickup unit 20.

Note that the optical unit 10 and the image pickup unit 20 may be simultaneously produced using a wafer level method. In other words, a plurality of optical wafers each including a plurality of optical members and a plurality of semiconductor wafers each including a plurality of semiconductor devices are stacked and are cut, to produce an image pickup unit with an optical unit. The optical unit 10 and the image pickup unit 20 produced using the above-described method are the same in size (dimensions in the direction perpendicular to the optical axis).

Figure 5:
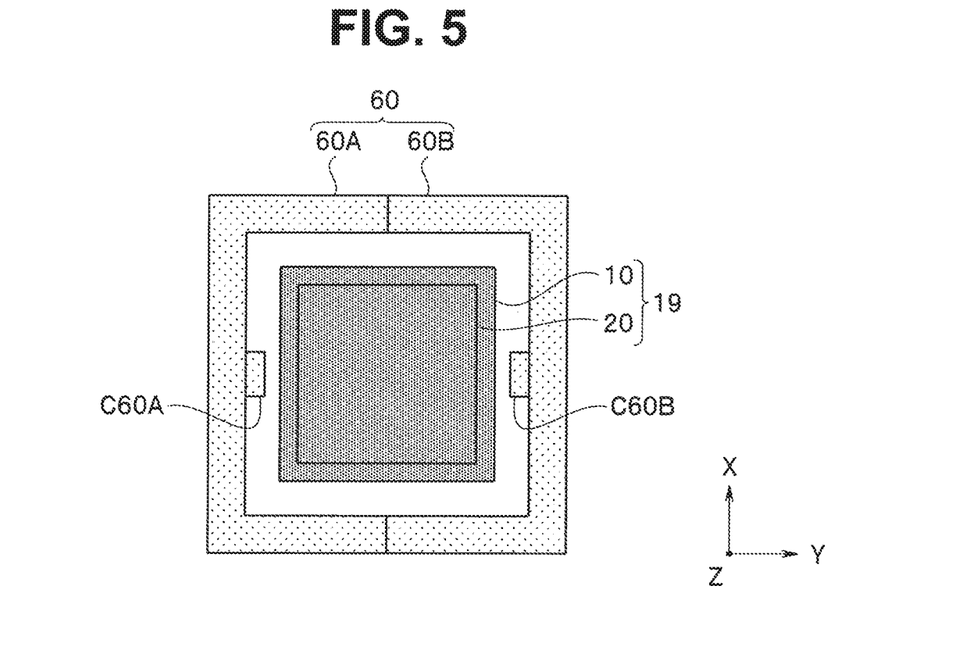
FIG. 5 is a top view for describing the method of manufacturing the image pickup apparatus according to the first embodiment.

<Step S12> Process for Arranging Unit in Mold

As illustrated in FIG. 5, the image pickup unit 20 with the optical unit 10 (hereinafter referred to as a "composite unit 19") is arranged in an internal space of the mold 60. The mold 60 includes a combination of two molds 60A and 60B, and an internal space hosing the composite unit 19 is formed within the mold 60. The mold 60 has protrusions C60A and C60B, respectively, on opposing wall surfaces of the mold 60.

A material for the mold 60 is not limited to metal, but may be silicon, as described below, for example.

Figure 6:
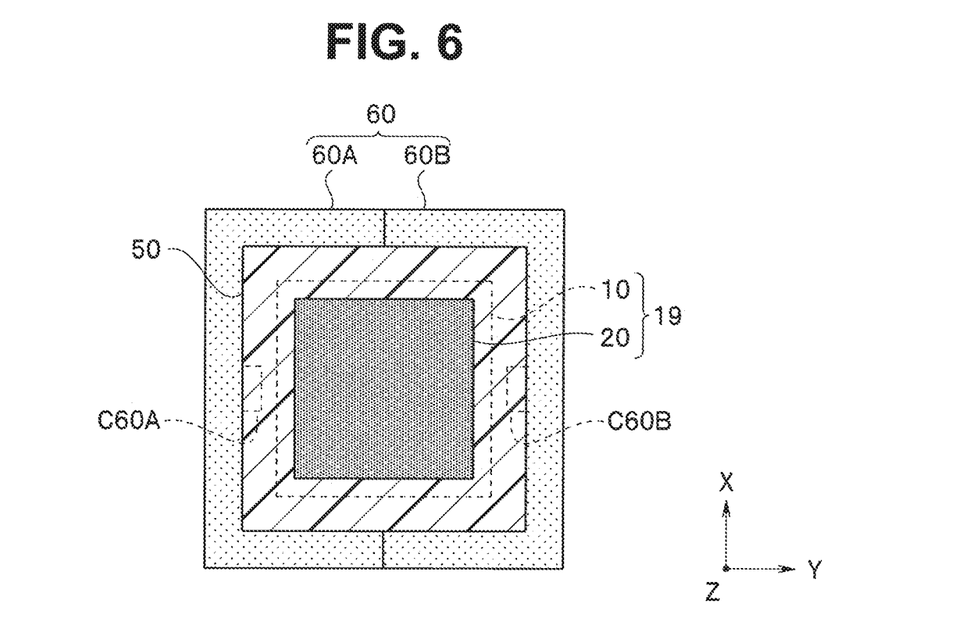
FIG. 6 is a top view for describing the method of manufacturing the image pickup apparatus according to the first embodiment.

<Step S13> Mold Resin Filling Process

As illustrated in FIG. 6, the mold 60 is filled with the mold resin 50. The mold resin 50 may be thermoplastic resin or thermosetting resin. For example, thermoplastic resin heated to a higher temperature than a melting point and fluidized is injected from an injection hole of a mold. Alternatively, thermosetting resin is injected into a heated mold, and is cured within the mold. Alternatively, two resin sheets may be molded with the composite unit 19 sandwiched between the resin sheets.

The mold resin 50 is made of resin such as epoxy, PA (polyamide), PC (polycarbonate), LCP (liquid crystal polymer), PEEK (polyether ether ketone), nylon, PPA (polyphthalamide), or ABS (acrylonitrile butadiene styrene resin), or the above-described resin into which an inorganic filler is mixed, for example.

Figure 7:
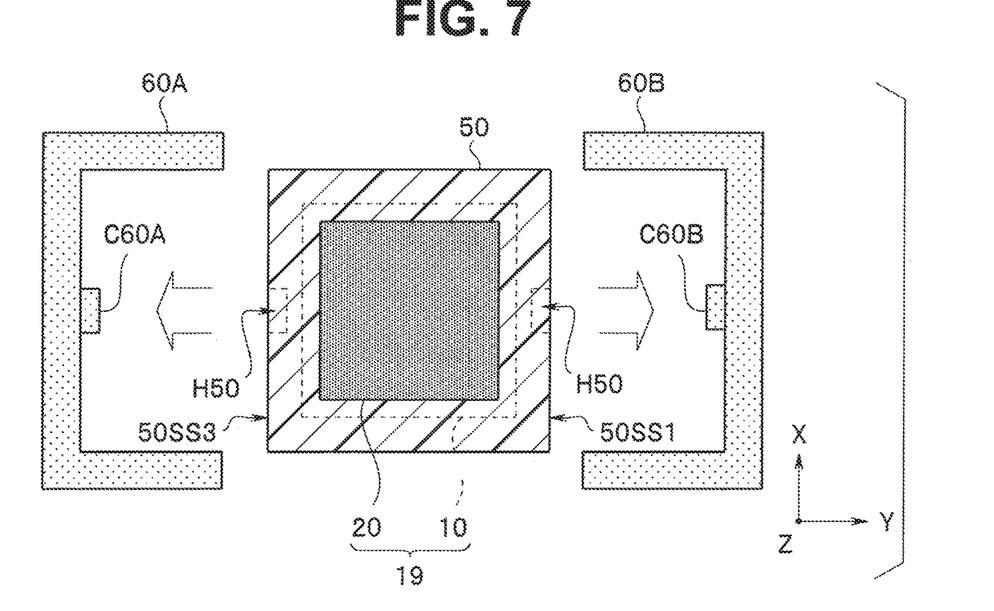
FIG. 7 is a cross-sectional view for describing the method of manufacturing the image pickup apparatus according to the first embodiment.

<Step S14> Process for Removal from Mold

As illustrated in FIG. 7, after the mold resin 50 is solidified, the mold 60 is divided into the mold 60A and the mold 60B, and the composite unit 19 is removed from the mold. Side surfaces 50SS1 and 50SS3 on both sides with the composite unit 19 sandwiched between the side surfaces 50SS1 and 50SS3 of the mold resin 50 onto which a shape of a wall surface of the internal space of the mold 60 has been transferred are respectively provided with recesses H50 as locking members.

Although an internal space of the recess H50 is circular columnar, the internal space may be conical or rectangular columnar, for example, if the mold resin 50 can be removed from the mold 60. Although the number of recesses H50 may be one, recesses may be preferably respectively provided on the side surfaces on both sides of the mold resin 50 to more stably hold the mold resin 50 by a jig 70 (see FIG. 8), as described below. The plurality of recesses H50 may differ in shape and size. The plurality of recesses H50 may be provided on one of the side surfaces.

Further, the mold resin 50 may be provided with a protrusion instead of or together with the recess H50. In other words, at least one locking member including at least one of a recess or a protrusion to which the jig 70 is fixed may be provided on an outer peripheral surface of the mold resin 50.

Although a depth of the recess H50 is set depending on a specification, the depth is preferably more than 50% and less than 90% of a thickness of the mold resin 50, for example. A cross section of the recess or the protrusion may be circular, rectangular, or polygonal, for example, if the jig 70 is fitted to the recess or the protrusion.

Note that a distance between the recess H50 of the mold resin 50 and the rear surface 20SB of the image pickup unit 20 is preferably shorter than a distance between the recess H50 and the emission surface 10SB of the optical unit 10, that is, the recess H50 is preferably provided in a region of the mold resin 50 covering the image pickup unit 20. If a size (a size in the direction perpendicular to the optical axis) of the image pickup unit 20 is smaller than a size of the optical unit 10, for example, the mold resin 50 covering the image pickup unit 20 is thick. Thus, the recess H50 having a predetermined depth required to hold the mold resin 50 is easily formed. In other words, the region of the mold resin 50 covering the image pickup unit 20 is preferably thicker than a region of the mold resin 50 covering the optical unit 10. If ultrasound bonding is performed, as described below, ultrasound energy can be efficiently applied to a bonding portion.

Figure 8:
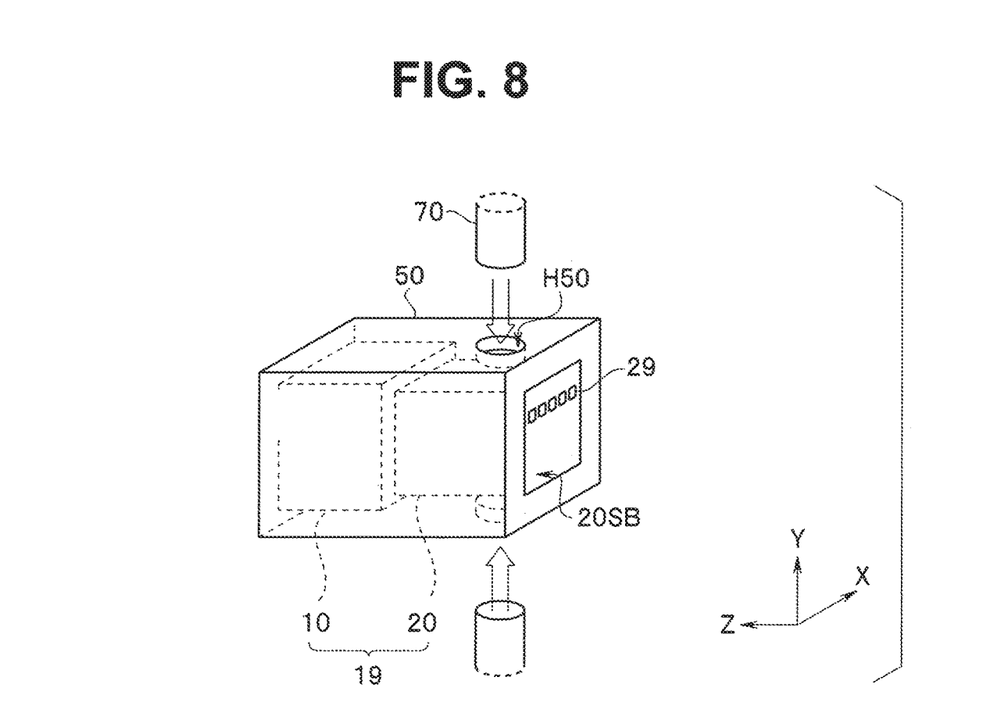
FIG. 8 is a perspective view for describing the method of manufacturing the image pickup apparatus according to the first embodiment.

<Step S15> Jig Attachment Process

As illustrated in FIG. 8, the jig 70 configured to hold the composite unit 19 having an outer peripheral surface covered with the mold resin 50 is attached to the composite unit 19.

If the jig 70 has a protrusion to be fitted to the recess H50, a shape of the jig 70 is not limited. For example, a planar portion of the jig 70 having the protrusion with a height lower than the depth of the recess H50 may abut on the outer peripheral surface of the mold resin 50.

Figure 9:
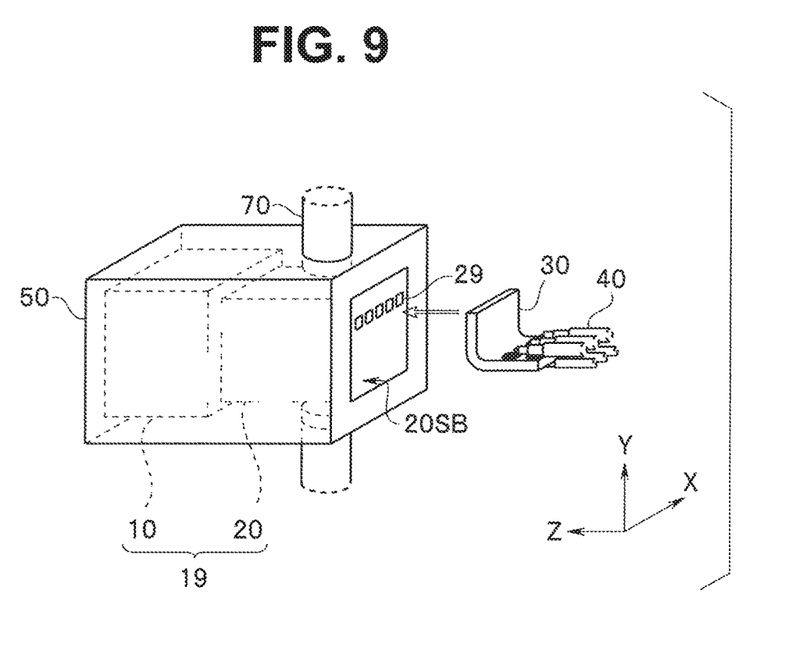
FIG. 9 is a perspective view for describing the method of manufacturing the image pickup apparatus according to the first embodiment.

<Step S16> Bonding Process

As illustrated in FIG. 9, the first electrode 31 in the wiring board 30 is bonded to the external electrode 29 in the image pickup unit 20. A bonding method is solder bonding, ultrasound bonding, or the like. Note that if the mold resin 50 covers the incidence surface 10SA of the optical unit 10 or the rear surface 20SB of the image pickup unit 20, the mold resin 50 covering the surfaces is removed before the bonding.

The composite unit 19 is reinforced by covering the outer peripheral surface with the mold resin 50. Further, the recess 1450 in the mold resin 50 and the jig 70 are fitted to each other. Accordingly, the composite unit 19 is stably held by the jig 70, and may not be damaged by the holding.

When the recess H50 in the mold resin 50 is formed on a side surface of the region covering the image pickup unit 20, the composite unit 19 can be firmly held at a position close to the bonding portion. Accordingly, if ultrasound bonding is performed, ultrasound power can be efficiently applied to the bonding portion.

Note that although the wiring board 30 to which the electrical cable 40 is bonded is bonded to the image pickup unit 20 in FIG. 9, the electrical cable 40 may be bonded to the wiring board 30 after the wiring board 30 is bonded to the image pickup unit 20.

Further, the electrical cable 40 may be directly bonded to the external electrode 29 in the image pickup unit 20 without via the wiring board. In other words, the wiring board 30 or the electrical cable 40 is bonded to the external electrode 29.

<Step S17> Jig Removal Process

The jig 70 is removed, and the image pickup unit 20 covered with the mold resin 50 is inserted into and fixed to a through hole of a distal end member (front frame) of the insertion section 3 in the endoscope 9.

Note that in the foregoing description, the composite unit 19 covered with the mold resin 50 has a substantially rectangular parallelepiped shape. However, the composite unit 19 covered with the mold resin 50 may have a substantially circular columnar shape or a substantially polygonal columnar shape (e.g., a hexagonal shape).

Modification to First Embodiment

Since an image pickup apparatus, an endoscope, and a method of manufacturing the image pickup apparatus (the image pickup apparatus and the like) in a modification are similar to and have the same effect as the effect of the image pickup apparatus 1 and the like according to the first embodiment already described, components having the same functions are respectively assigned the same reference numerals and hence, description of the components is omitted.

<Modification 1>

Figure 10:
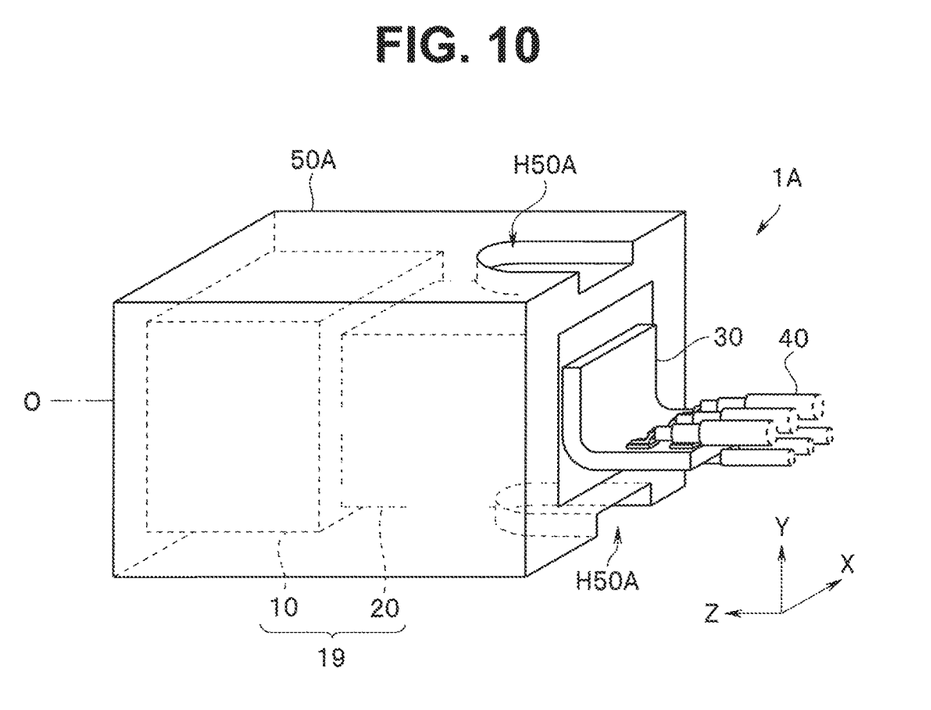
FIG. 10 is a perspective view of an image pickup apparatus according to a modification 1 to the first embodiment.

As illustrated in FIG. 10, a recess H50A in mold resin 50A in an image pickup apparatus 1A in a modification 1 is provided to extend to a rear end of the mold resin 50A, and a size in a cross section in a direction perpendicular to an optical axis of the recess H50A is the same toward the rear end.

Figure 11:
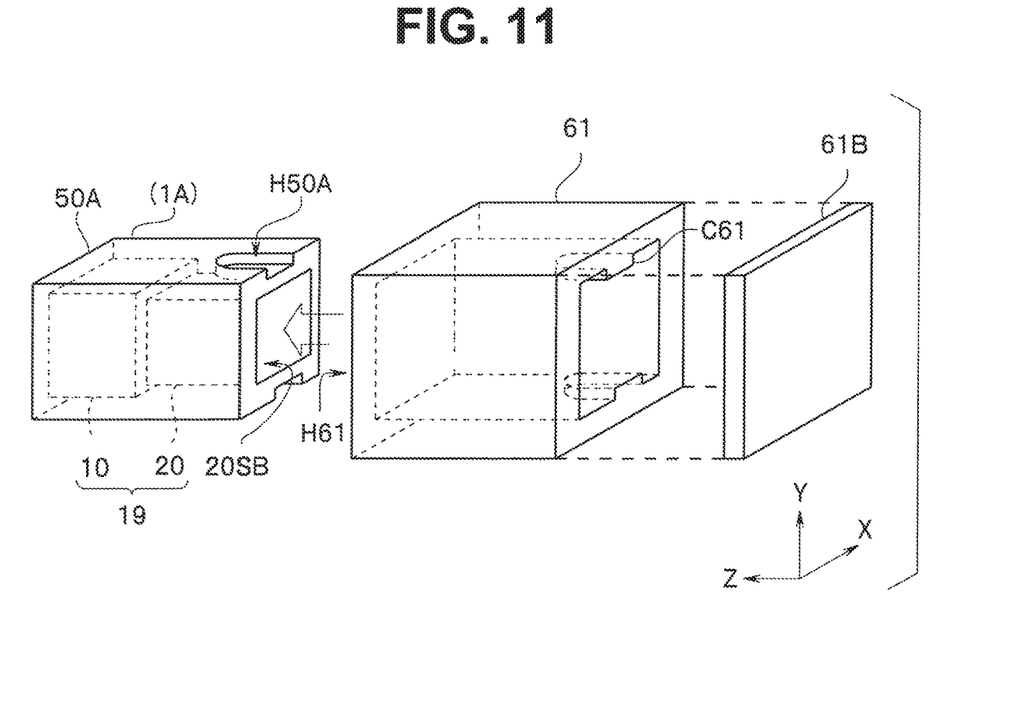
FIG. 11 is a perspective view for describing a method of manufacturing the image pickup apparatus according to the modification 1 to the first embodiment.

As illustrated in FIG. 11, a protrusion C61 exists on an inner surface of a mold 61 configured to mold the mold resin 50A in the image pickup apparatus 1A. The protrusion C61 is provided to extend to a rear end of the mold 61, and a size in a cross section in the direction perpendicular to the optical axis of the protrusion C61 is the same. Four outer peripheral surfaces of the mold resin 50A are parallel to a direction of the optical axis.

Accordingly, a process for removing the mold 61 is a process for pulling out an optical unit 10 and an image pickup unit 20 covered with the mold resin 50A, which are disposed in a hole H61 in the mold 61.

Note that a bottom surface section 61B is separated from the mold 61 to clearly indicate a structure of the mold in FIG. 11. However, the bottom surface section 61B is integral with and need not be separated from the mold 61. In other words, the mold 61 may be an integral object having the hole H61.

A recess H50A may have a shape, a part of which is fitted to a jig.

To remove mold resin provided with a protrusion from a mold, two molds are combined with each other when used, and the combined molds need to be disassembled after being filled with resin.

The image pickup apparatus 1A is easy to manufacture because the mold 61 can be removed without being disassembled. Needless to say, the size in a cross section in the direction perpendicular to the optical axis of the recess H50A as a locking member may expand toward a rear end of the mold 61. In this case, the mold 61 is easily pulled out of the mold resin 50A.

Second Embodiment

Since an image pickup apparatus and the like according to the present embodiment are similar to and have the same effect as the effect of the image pickup apparatus 1 and the like according to the first embodiment already described, components having the same functions are respectively assigned the same reference numerals and hence, description of the components is omitted.

Figure 12:
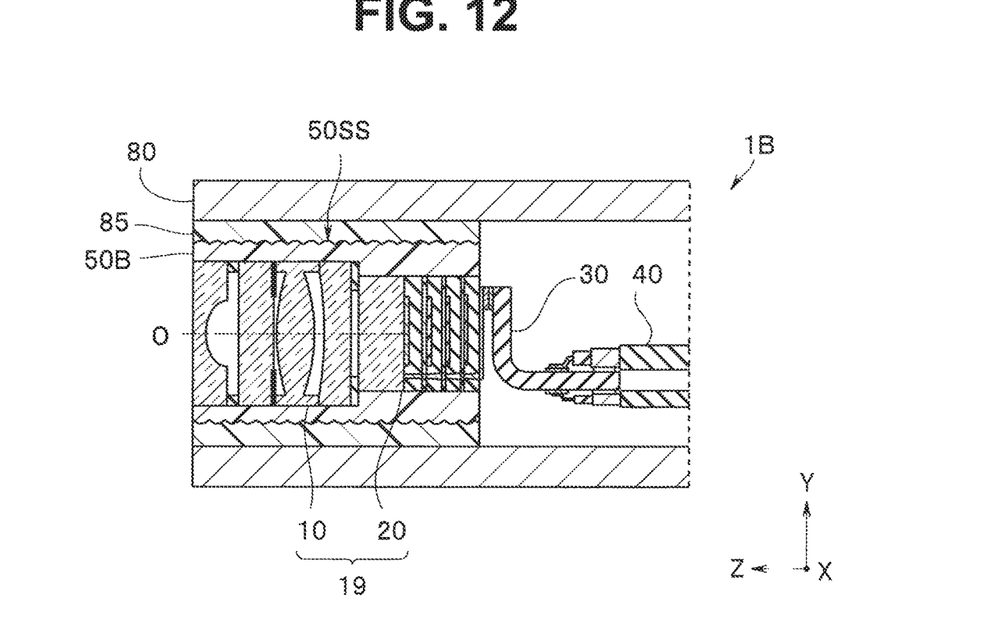
FIG. 12 is a cross-sectional view of an image pickup apparatus according to a second embodiment.

As illustrated in FIG. 12, an image pickup apparatus 1B according to the present embodiment includes a cylindrical housing 80 and adhesive resin 85 in addition to components in the image pickup apparatus 1. A composite unit 19 having an outer peripheral surface covered with mold resin 50B is inserted into the cylindrical housing 80. The adhesive resin 85 is disposed between the housing 80 and the mold resin 50B.

In the image pickup apparatus 1B, an outer surface 50SS of the mold resin 50B is a periodically stepped uneven surface. Adhesion of the mold resin 50B to the adhesive resin 85 is improved due to an anchor effect by the uneven surface.

An inner surface shape of a mold is transferred onto a shape of the outer surface 50SS of the mold resin 50B. In other words, when an inner surface of the mold is an uneven surface, the mold resin 50B having the uneven surface is produced.

Figure 13:
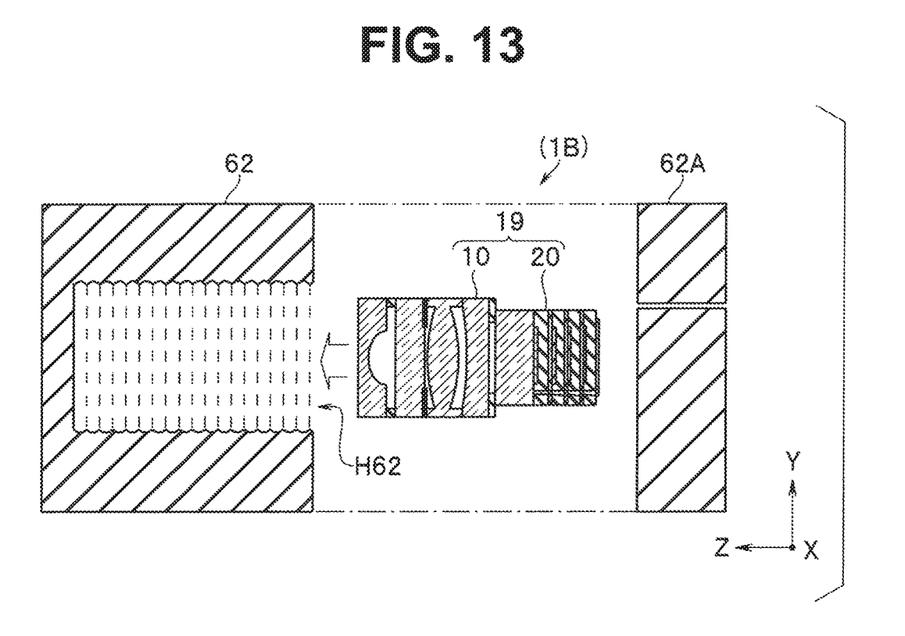
FIG. 13 is a cross-sectional view for describing a method of manufacturing the image pickup apparatus according to the second embodiment.

For example, a silicon substrate 62 having a hole H62 formed using a Bosch process is used as a mold, as illustrated in FIG. 13. The hole H62 into which the composite unit 19 is inserted is closed by a mold 62A having a resin injection hole, to form a space into which mold resin is injected.

In a bosh process as one type of a reactive ion etching (RIE) method, isotropic etching and protective film deposition are repeatedly performed. Unevenness, the number of which corresponds to the number of times of switching between etching and protective film deposition, which is referred to as "scallop", are formed on a wall surface of the hole H62 formed using a Bosch process. Since a switching period between etching and protective film deposition is constant, unevenness having a predetermined period are formed on an inner surface of the hole.

A periodically stepped surface formed by transferring a wall surface shape of the hole H62 formed using a Bosch process is accurately defined because a maximum height (Rz: JIS B 0601 2001) is more than 0.001 μm and less than 0.1 μm and a spacing (a period) between a convexity and a concavity is more than 0.1 μm and less than 10 μm.

An uneven surface of the mold resin 50B is preferably a periodically stepped surface formed by transferring a wall surface shape of the hole H62 produced using a Bosch process.

Third Embodiment

Since respective image pickup apparatuses and the like according to a third embodiment and a modification to the third embodiment are similar to and have the same effect as the effect of the image pickup apparatus 1 and the like already described, components having the same functions are respectively assigned the same reference numerals and hence, description of the components is omitted.

In the image pickup apparatus and the like according to the first embodiment, the wiring board 30 is bonded to the composite unit 19 protected by the mold resin 50. However, a method of protecting the composite unit 19, which is not high in mechanical strength, at the time of bonding the wiring board is not limited to coating with the mold resin 50.

Figure 14:
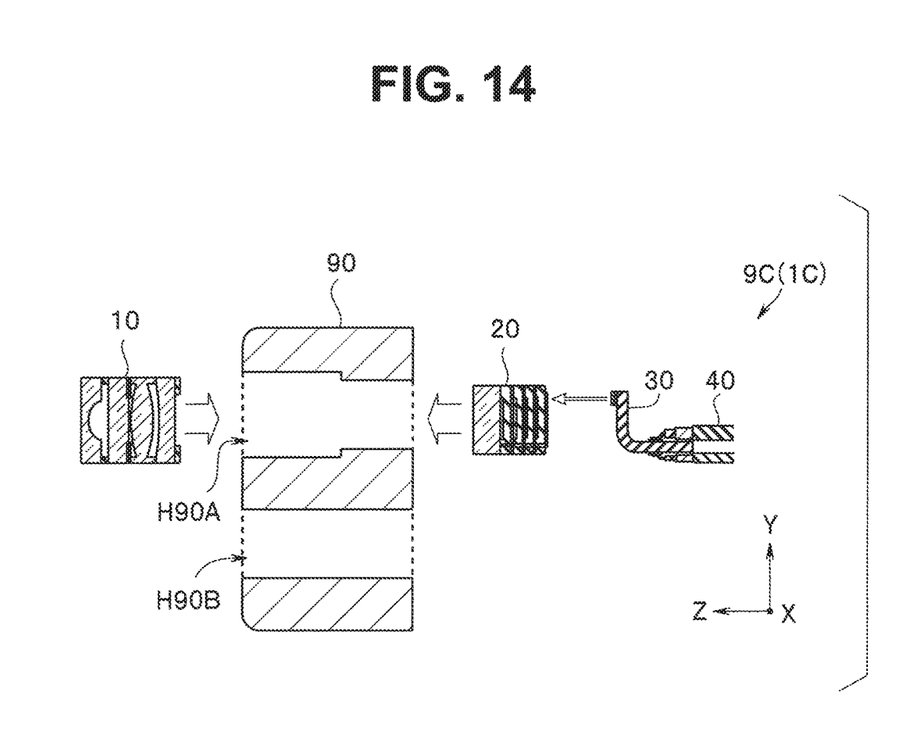
FIG. 14 is a cross-sectional view for describing a method of manufacturing an image pickup apparatus according to a third embodiment.

As illustrated in FIG. 14, after an image pickup apparatus 1C according to a third embodiment is inserted into a through hole H90A in a distal end member (front frame) 90 in a distal end portion 3A of an endoscope 9C, a wiring board 30 is bonded.

For example, the distal end member 90 composed of stainless steel includes the through hole H90A into which the image pickup apparatus 1C is inserted and a through hole H90B into which a treatment instrument channel has been inserted.

An optical unit 10 is inserted from a front opening of the through hole H90A, an image pickup unit 20 is inserted from a rear opening of the through hole H90A, and the optical unit 10 and the image pickup unit 20 are each fixed to the through hole H90A with an adhesive agent or the like (not illustrated). The wiring board 30 is bonded to the image pickup unit 20 inserted into and protected by the distal end member 90.

Modification 1 to Third Embodiment

Figure 15:
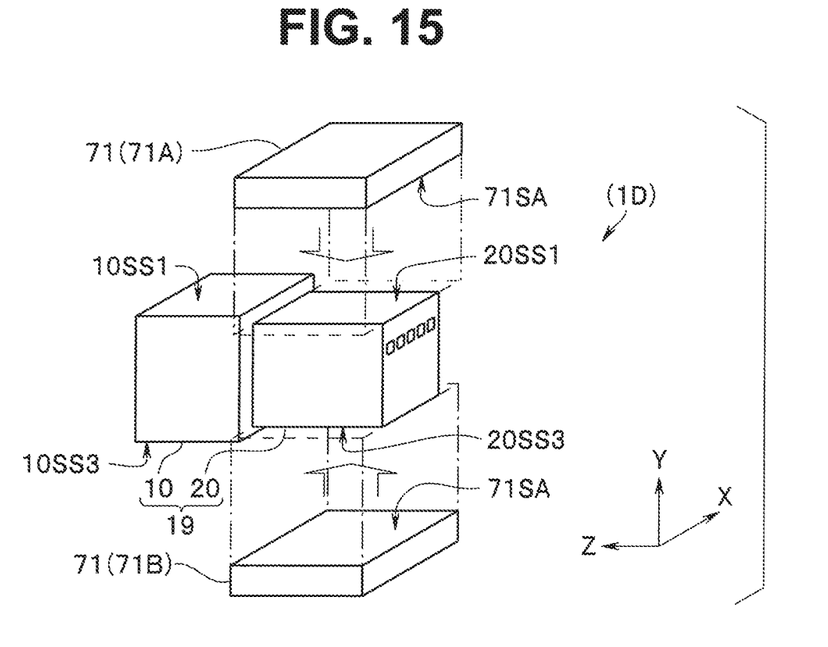
FIG. 15 is a perspective view for describing a method of manufacturing an image pickup apparatus according to a modification 1 to the third embodiment.

As illustrated in FIG. 15, in an image pickup apparatus ID according to the present modification, side surfaces 20SS1 and 20SS3, which face each other, of an image pickup unit 20 are sandwiched between respective holding surfaces 71SA of jigs 71 (71A and 71B) in a bonding process.

Note that if a composite unit 19 has at least two surfaces, which face each other, respectively held by the jigs, the composite unit 19 may not be damaged at the time of bonding a wiring board. In other words, surfaces to be held by the jigs may be respectively side surfaces 10SS1 and 10SS3 arranged with an optical unit 10 sandwiched between the side surfaces 10SS1 and 10SS3.

Modification 2 to Third Embodiment

Figure 16:
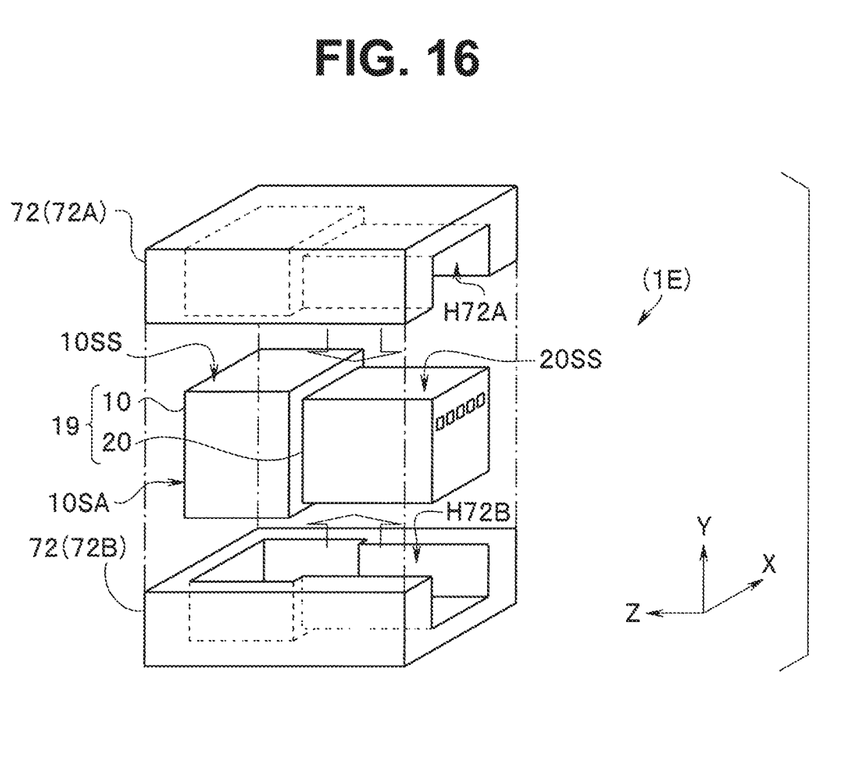
FIG. 16 is a perspective view for describing a method of manufacturing an image pickup apparatus according to a modification 2 to the third embodiment.

As illustrated in FIG. 16, in an image pickup apparatus 1E according to the present modification, not only four side surfaces 20SS of an image pickup unit 20 but also an incidence surface 10SA and four side surfaces 10SS of an optical unit 10 are housed in a space firmed by respective recesses H72A and H72B of jigs 72 (72A and 72B), and abut on a wall surface of the space.

Note that only the four side surfaces 20SS1 to 20SS4 of the image pickup unit 20 may be held in the space formed by the jigs.

The composite unit 19, which is not high in mechanical strength, may not be damaged if protected by another member in the bonding process.

Modification 3 to Third Embodiment

Figure 17:
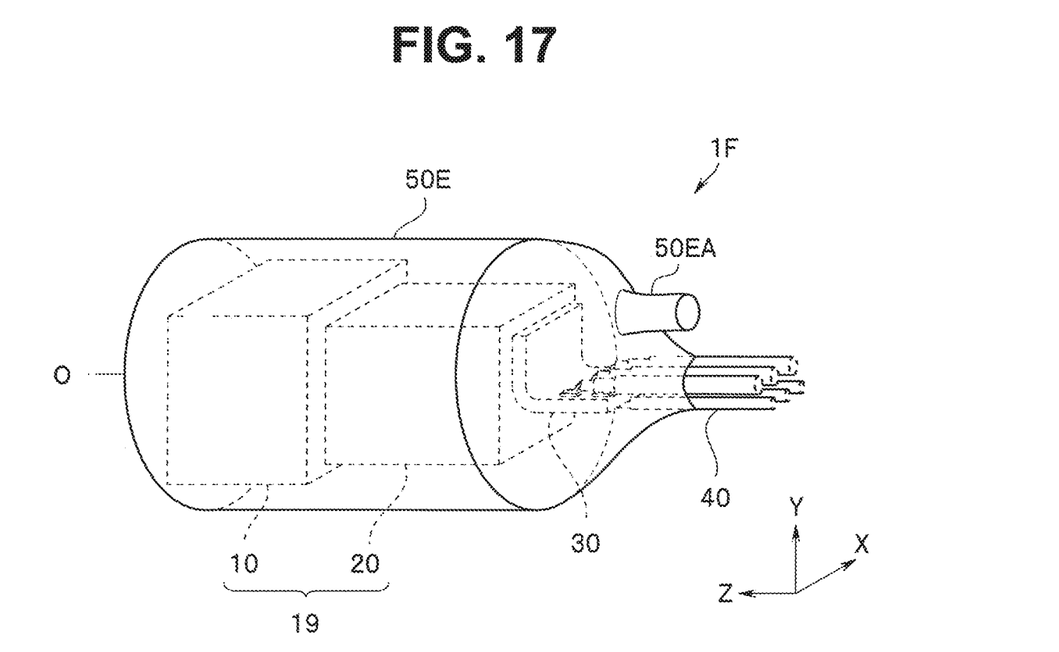
FIG. 17 is a perspective view for describing a method of manufacturing an image pickup apparatus according to a modification 3 to the third embodiment.

As illustrated in FIG. 11, in an image pickup apparatus 1F according to the present modification, a composite unit 19 is protected by another member in a bonding process, and a wiring board 30 is bonded. After the bonding process, mold resin 50E configured to protect the composite unit 19 is disposed.

The mold resin 50E covers not only a side surface of the composite unit 19 but also a bonding portion between an external electrode 29 and the wiring board 30 and a bonding portion between the wiring board 30 and an electrical cable 40. The composite unit 19 protected by the mold resin 50E has a circular columnar shape that is circular in cross section in a direction perpendicular to an optical axis.

The mold resin 50E is disposed by being injected from a resin injection portion in a rear part of a mold. The mold resin 50E includes a protrusion 50EA formed by the resin injection portion being filled with resin. However, the protrusion 50EA is positioned within a space obtained by extending an incidence surface 10SA of an optical unit 10 in a direction of the optical axis. Thus, an outer diameter of the image pickup apparatus does not increase.

The present invention is not limited to the above-described embodiments and the like, but various changes, alterations, and the like are possible without departing from the scope and spirit of the invention.

What is claimed is:

1. An image pickup apparatus disposed in an endoscope, the image pickup apparatus comprising:
    an optical unit in which a plurality of optical members are stacked;
    an image pickup unit including an image pickup sensor and a plurality of semiconductor devices;
    one of a wiring board or an electrical cable bonded to the image pickup unit; and
    mold resin covering a side surface of a composite unit including the optical unit and the image pickup unit;
    wherein the mold resin including at least one locking member comprising at least one of a recess or a protrusion formed on an outer peripheral surface of the mold resin.

2. image pickup apparatus according to claim 1, wherein the at least one locking member is provided in a region of the mold resin covering the image pickup unit.

3. The image pickup apparatus according to claim 2, wherein
    the image pickup unit is smaller in size in a direction perpendicular to an optical axis than the optical unit, and
    the outer peripheral surface of the mold resin is parallel to a direction of the optical axis.

4. The image pickup apparatus according to claim 2, wherein a region of the mold resin covering the image pickup unit is thicker than a region of the mold resin covering the optical unit.

5. The image pickup apparatus according to claim 1, wherein the at least one locking member extends to a rear end of the mold resin.

6. The image pickup apparatus according to claim 5, wherein a size of the at least one locking member in a cross section in a direction perpendicular to an optical axis increases toward the rear end.

7. The image pickup apparatus according to claim 1, wherein the at least one locking member comprises a plurality of locking members.

8. The image pickup apparatus according to claim 7, wherein the plurality of locking members comprises first and second locking members respectively provided on opposing sides of the mold resin, the opposing sides sandwiching the composite unit.

9. The image pickup apparatus according to claim 7, wherein the plurality of locking members differ in shape and size.

10. The image pickup apparatus according to claim 1, wherein the at least one locking member is fitted in a jig configured to hold the composite unit.

11. A method of manufacturing an image pickup apparatus disposed in an endoscope, the method comprising:
    producing an optical unit in which a plurality of optical members are stacked and producing an image pickup unit including an image pickup sensor and a plurality of semiconductor devices;
    arranging a composite unit including the optical unit and the image pickup unit within a mold;
    filling the mold with mold resin;
    removing the composite unit covered with the mold resin from the mold to provide the mold resin with at least one locking member comprising at least one of a recess or a protrusion formed on an outer peripheral surface of the mold resin;
    fixing a jig to the at least one locking member to hold the composite unit covered with the mold resin;
    while the composite unit covered by the mold resin is held by the jig, bonding the image pickup unit in the composite unit to one of a wiring board or an electrical cable; and
    subsequent to the bonding, removing the jig fixed to the composite unit covered with the mold resin from the at least one locking member.

12. The method of manufacturing the image pickup apparatus according to claim 11, wherein
    the locking member extends to a rear end of the mold resin, and a size of the at least one locking member in a cross section in a direction perpendicular to an optical axis one of increases toward the rear end or is a same size, and
    the removing of the composite unit covered with the mold resin from the mold comprises moving the composite unit relative to the mold along the optical axis.

13. An endoscope comprising:
    an image pickup apparatus, the image pickup apparatus comprising:
        an optical unit in which a plurality of optical members are stacked;
        an image pickup unit including an image pickup sensor and a plurality of semiconductor devices;
        one of a wiring board or an electrical cable bonded to the image pickup unit; and
        mold resin covering a side surface of a composite unit including the optical unit and the image pickup unit;
        wherein the mold resin having at least one locking member comprising at least one of a recess or a protrusion formed on an outer peripheral surface of the mold resin.

* * * * *